United States Patent
Kawai

(10) Patent No.: US 6,200,928 B1
(45) Date of Patent: Mar. 13, 2001

(54) EFFERVESCENT PREPARATION FOR PLANTS

(76) Inventor: Hiroshi Kawai, 25-3-305, Nakata-higashi 2-chome, Izumi-ku, Yokohama-shi, Kanagawa 245 (JP)

(*) Notice: Subject to any disclaimer, the term of this patent is extended or adjusted under 35 U.S.C. 154(b) by 0 days.

(21) Appl. No.: 09/180,265

(22) PCT Filed: May 6, 1997

(86) PCT No.: PCT/JP97/01521
§ 371 Date: Nov. 6, 1998
§ 102(e) Date: Nov. 6, 1998

(87) PCT Pub. No.: WO97/41732
PCT Pub. Date: Nov. 13, 1997

(30) Foreign Application Priority Data

May 7, 1996 (JP) .................................................. 8-112811

(51) Int. Cl.[7] ............................ A01N 25/16; A01N 25/02
(52) U.S. Cl. ............................... 504/116; 504/113; 424/43
(58) Field of Search ................................... 504/116; 71/26

(56) References Cited

U.S. PATENT DOCUMENTS 5,549,729 * 8/1996 Yamashita ................................. 71/26
5,582,627 * 12/1996 Yamashita ................................. 71/26

* cited by examiner

*Primary Examiner*—S. Mark Clardy
*Assistant Examiner*—Konata M George
(74) *Attorney, Agent, or Firm*—Ostrolenk, Faber, Gerb & Soffen, LLP

(57) ABSTRACT

The present invention discloses an effervescent preparation for plants comprising a solid composition containing at least carbonate and/or hydrogencarbonate, water-soluble solid acid, yeast extract and/or methionine. As a result, the present invention is able to provide an effervescent preparation for plants that can be easily dissolved and diffused when applying to a field, has good storage stability by being resistant to putrefaction and deterioration caused by contamination by sundry germs in comparison with the case of dissolving in water and so forth, is handled easily, and can be applied to watered rice paddies directly by throwing, thereby enabling shortening of working time and conservation of manpower.

2 Claims, No Drawings

EFFERVESCENT PREPARATION FOR PLANTS

TECHNICAL FIELD

The present invention relates to an effervescent preparation for plants, and more particularly, to an effervescent preparation for plants in the form of effervescent granules, effervescent tablets and so forth.

BACKGROUND ART

In recent years, research has been conducted on methods for efficiently generating the plant hormone, ethylene, having various physiological effects, by spraying or irrigating plants with one or more types of substances selected from yeast extracts extracted from yeast or methionine (The Society for Chemical Regulation of Plants (1993), Abstract of Research Presentations, p. 114–115 and Japanese Patent Laid-Open Publication No. Hei7-285816) . In addition, it has been clearly demonstrated that dissolving one or more types of substances selected from yeast extracts or methionine and sprinkling on rice stems and leaves or irrigating underground areas has the effect of promoting the generation of phytoalexin and inhibiting rice blast (specification of Japanese Patent Application No.Hei7-353132, Bioscience, Biotechnology, and Agrochemistry, 1997, Vol. 71, p. 125).

However, since typically obtainable yeast extracts are in the form of dry fine powders and pellets, when applying to a field, they must first be dissolved in a suitable solvent such as water, thereby resulting in the problem of requiring both time and trouble for their dissolution and spraying. In addition, in the case of dissolving powdered yeast extract in water, and in the case of a yeast extract being obtained not in the form of a powder but rather in the form of a solution by dissolving in a suitable solvent such as water in advance, there were disadvantages in terms of storage caused by contamination by sundry germs making the liquid susceptible to putrefaction and deterioration.

In addition, methionine, a precursor of ethylene that is known to further increase ethylene production either by using alone or by mixing with yeast extract (Japanese Patent Laid-Open Publication No.Hei7-285817), also has poor solubility and diffusivity resulting in the problem of requiring considerable time and trouble in the case of using by dissolving in water.

On the other hand, rice paddy herbicidal tablets or capsules containing herbicide ingredients, surface active agents, foaming agents, binders and so forth (Japanese Patent Laid-Open Publication No.Hei3-223203), effervescent agricultural chemical preparations for application to rice paddies consisting of agricultural chemical active ingredients, carbonates, water-soluble solid acids and high boiling point solvents (Japanese Patent Laid-Open Publication No.Hei5-85901) and stabilized effervescent agricultural chemical preparations consisting of agricultural chemical active ingredients, carbonates or hydrogencarbonates, solid acids and boric oxide (Japanese Patent Laid-Open Publication No.Hei6-211604) have been proposed.

The object of the present invention is to provide an effervescent preparation for plants using yeast extract in the form of dry fine powder or pellets that can be easily dissolved and diffused when applying to a field, which has good storage stability by being resistant to putrefaction and deterioration caused by contamination by sundry germs in comparison with the case of dissolving in water and so forth, is handled easily, and can be applied to watered rice paddies directly by throwing, thereby enabling shortening of working time and conservation of manpower.

Moreover, another object of the present invention is to provide an effervescent preparation for plants containing methionine, which has poor solubility and diffusivity in water in the same manner as yeast extract, either alone or as a mixture with yeast extract, which in addition to having characteristics like those described above, is able to eliminate the trouble of dissolving in water.

DISCLOSURE OF THE INVENTION

As a result of earnest research on the above problems, the inventor of the present invention found that the above problems can be solved by forming an effervescent preparation for plants, comprising a solid composition containing yeast extract and/or methionine, carbonate and/or hydrogencarbonate and water-soluble solid acid, into the form of, for example, granules or tablets, said effervescent preparation for plants reacting when thrown into water to produce carbon dioxide gas enabling the contained yeast extract and methionine to be dissolved and diffused both easily and uniformly, thereby leading to completion of the present invention.

Namely, the present invention is an effervescent preparation for plants comprising a solid composition containing at least carbonate and/or hydrogencarbonate, water-soluble solid acid, yeast extract and/or methionine.

In addition, the present invention is an effervescent preparation for plants as described above that contains at least one type of substance selected from agricultural chemical active ingredients, fertilizer ingredients and surface active agents.

BEST MODE FOR CARRYING OUT THE INVENTION

The following provides a detailed explanation of the present invention.

There are no particular limitations on the carbonates or hydrogencarbonates used in the present invention, specific examples of which include sodium carbonate, potassium carbonate, calcium carbonate, ammonium carbonate, sodium sesquicarbonate, sodium hydrogencarbonate, potassium hydrogencarbonate, ammonium hydrogencarbonate, potassium sesquicarbonate, ammonium sesquicarbonate, lithium carbonate and lithium hydrogencarbonate and so forth, while particularly preferable examples include sodium hydrogencarbonate and sodium carbonate. These carbonates or hydrogencarbonates may be used alone or as a combination of two or more types in an arbitrary ratio.

In addition, there are no particular limitations on the water-soluble solid acids used in the present invention, specific examples of which include citric acid, maleic acid, succinic acid, malic acid, ascorbic acid, fumaric acid, tartaric acid, oxalic acid, malonic acid, adipic acid, boric acid, sodium dihydrogenphosphate and potassium dihydrogenphosphate, while preferable examples include citric acid, maleic acid, malic acid, ascorbic acid, fumaric acid and sodium dihydrogenphosphate. These water-soluble solid acids may be used alone or as a combination of two or more types in an arbitrary ratio.

The total content of carbonates and/or hydrogencarbonates and water-soluble solid acids is within the range of 5 to 99.999 wt %, preferably 10 to 90 wt %, and more preferably 20 to 80 wt %, relative to the total weight of the effervescent preparation for plants of the present invention. In addition, the weight ratio of carbonates and/or hydrogencarbonates to water-soluble solid acids is within the range of 1:10 to 10:1, and preferably 3:7 to 7:3. If the weight ratio exceeds the range of 1:10 to 10:1, the amount of carbon dioxide gas generated during the reaction decreases resulting in poor diffusion of other ingredients. Moreover, this is also not preferable since the property of the dissolved water becomes strongly acidic or alkaline easily.

The yeast extract used in the present invention is obtained by performing extraction on yeast using a suitable extraction solvent such as alcohol and then drying. There are no particular limitations on the yeast species, culturing conditions or drying conditions and so forth. Specific examples of yeast extracts used in the present invention include commercially available yeast extract for microbial culturing and yeast extract for food additives.

Although varying according to the object of use and usage method, the content of these yeast extracts is within the range of 0.001 to 80 wt %, preferably 0.01 to 50 wt %, and more preferably 0.1 to 30 wt%, relative to the total weight of the effervescent preparation for plants of the present invention. If the total content is less than 0.001 wt %, variation of ingredients tend to occur easily in terms of production, thereby making this undesirable. In addition, if the total content exceeds 80 wt %, solubility and diffusivity become poor, thereby making this also undesirable.

In addition, binders, mineral fine powders, absorbent fine powders, decomposition inhibitors, lubricants, colorants, thickeners, disintegrating agents, desiccants and chemical toxicity alleviators can be suitably contained in the effervescent preparation for plants of the present invention over a range that does not significantly impair the solubility and diffusivity in water of the above yeast extract.

Examples of binders include starch, starch derivative, lactose, dextrin, polyethylene glycol, carboxymethylcellulose, gum arabic, traganth gum, xanthan gum, polyvinylpyrrolidone and polyvinyl alcohol and so forth. Examples of mineral fine powders include talc, clay, bentonite and diatomaceous earth. Examples of absorbent fine powders include white carbon.

Although L-methionine, D-methionine or DL-methionine may be used for the methionine used in the present invention, it is preferable to use DL-methionine in consideration of its low price. Methionine is a type of naturally occurring amino acid. When applied to plants by spraying, irrigating or immersing and so forth, it is metabolized inside the plant and known to form ethylene, a substance having various physiological actions. In addition, methionine is also known to be one of the least expensive of the more than 20 types of amino acids, and is also contained in livestock feed and so forth.

Although varying according to the object of use and usage method, the content of methionine is within the range of 0.01 to 80 wt %, preferably 0.1 to 60 wt %, and more preferably 1 to 40 wt %, relative to the total weight of the effervescent preparation for plants of the present invention. If the methionine content is less than 0.01 wt %, effects are not remarkable thus making this undesirable. In addition, if the methionine content exceeds 80 wt %, solubility and diffusivity become poor, thereby making this also undesirable.

There are no particular limitations on the agricultural chemical active ingredients used in the present invention. Specific examples are listed below. In addition, these agricultural chemical active ingredients may be used alone or as a combination of two or more types in an arbitrary ratio. Furthermore, the generic names contained in the Agricultural Chemical Handbook (published by the Japan Plant Protection Association, 1989) are used for the names of the agricultural chemical active ingredients listed below.

The following are examples of agricultural chemical active ingredients used as herbicide active ingredients:

2,4-D, MCP, MCPB, CNP, MCC, DCPA, ACN, MCPA-thioethyl, Clomeprop, Naproanilide, Chlomethoxyfen, Thiobencarb, Bifenox, Esprocarb, Molinate, Dimepiperate, Butachlor, Pretilachlor, Bromobutide, Mefenacet, Daimuron, Bensulfuron-methyl, Simetryn, Prometryn, Dimethametryn, Bentazone, Oxadiazon, Pyrazolynate, Pyrazoxyfen, Benzofenap, Trifluralin and Piperophos.

The following are examples of agricultural chemical active ingredients used as insecticide active ingredients:

BRP, CVMP, PMP, PAP, DEP, EPN, NAC, MTMC, MIPC, BPMC, PHC, MPMC, XMC, MPP, MEP, Pirimiphos-methyl, Diazinon, Isoxathion, Pyridaphenthion, Chlorpyrifos-methyl, Vamidothion, Malathion, Dimethoate, Disulfoton, Monocrotophos, Dimethylvinphos, Propaphos, Bendiocarb, Carbosulfan, Bendiocarb, Thiodicarb, Cycloprothrin, Etofenprox, Cartap, Thiocyclam, Bensultap and Buprofezin.

The following are examples of agricultural chemical active ingredients used as germicide active ingredients:

Basic copper sulfate, basic copper chloride, cupric hydroxide, organic sulfur nickel salts, Thiram, Captan, TPN, Phthalide, IBP, EDDP, Thiophanate-methyl, Benomyl, Iprodione, Mepronil, Flutolnil, Tecloftalam, Pencycuron, Metalaxyl, Triflumizole, Blastcidin S, Kasugamycin, Polyoxins, Validamycin A, Oxytetracycline, Hymexazol, Methasulfocarb, MAF, MAFE, benthiazole, phenazine oxide, Diclomezine, Probenazole, Isoprothiolane, Tricyclazole, Pyroquilon, Oxolinic acid and Iminoctadine.

In addition, plant growth regulation ingredients such as Inabenfide, oxyethylenedocosanol, nicotinic amide and benzylaminopurine can be added as necessary to the effervescent preparation for plants of the present application in addition to the agricultural chemical active ingredients listed above.

In the case the agricultural chemical active ingredient is a liquid or in a liquid state as a result of adding a solvent other than water, the agricultural chemical active ingredient can be used after adsorbing onto a powdered oiling carrier such as silicic acid. In addition, in the case these agricultural chemical active ingredients have a low melting point, high boiling point solvents such as fatty acid alcohol esters, polybasic acid alcohol esters, polyvalent alcohol fatty acid esters and higher alcohols can be added to prevent crystallization. Although varying according to the type of active ingredient, the amount of these agricultural chemical active ingredients is typically within the range of 0.1 to 60 wt %, and preferably 10 to 50 wt %, relative to the effervescent preparation for plants of the present invention.

There are no particular limitations on the fertilizer ingredients used in the present invention. Specific examples are listed below.

Compost, manure, livestock excreta, human excreta, burned plant ash, wood ash, rice straw, barley straw, rice chaff, rice bran, wheat bran, bean pods, nitrogenous fertilizers, phosphate fertilizers, potash fertilizers, composite fertilizers, calcareous fertilizers, silicate fertilizers, magnesia fertilizers, manganese fertilizers, boron fertilizers, trace element composite fertilizers, organic fertilizers, fish dregs, livestock and poultry feces, processed livestock and poultry feces, ashed livestock and poultry feces, sludge fertilizers, sugar by-product lime, converter slag, ashed shell powder, agricultural product waste, food industry waste, fermentation industry waste, fermentation lees, fiber industry waste, marine product industry waste, sewer sludge, urban compost and ashed bone. These fertilizer ingredients may be used alone or as a combination of two or more types in an arbitrary ratio.

In addition, soil improvers such as zeolite, bentonite, vermiculite, peat, pearlite, corrosive acid materials, charcoal, polyethyleneimine materials and polyvinyl alcohol materials can be mixed in addition to these fertilizer ingredients. Using the dried raw materials of these fertilizer ingredients is more advantageous in terms of production of the preparation. Although varying according to the type of fertilizer ingredient, object of use and usage method, the amount of these fertilizer ingredients is typically within the range of 0.1 to 90 wt %, and preferably 1 to 50 wt % relative to the weight of the effervescent preparation for plants of the present invention.

Examples of surface active agents used in the present invention include anionic surface active agents such as alkylsulfosuccinates, condensed phosphates, alkylbenzenesulfonates such as sodium dodecylbenzenesulfonate, alkylnaphthalene sulfonates, formalin condensation products of naphthalene sulfonates, lignin sulfonates, polycarboxylates, alkylether sulfates, polyoxyethylene alkylarylphenyl ether sulfates, polyoxyethylene alkylaryl ether sulfates, polyoxyethylene alkylaryl sulfates, polyoxyethylene alkylaryl ether sulfate esters and polyoxyethylene alkylaryl ether acetate ester sulfates. Examples of their salts include alkaline metal salts, ammonium salts and amine salts.

Moreover, examples of nonionic surface active agents include polyoxyethylene alkyl ether, polyoxyethylene alkylaryl ether, polyoxyethylene alkylarylphenyl ether, polyoxyethylene styrylphenyl ether, polyoxyethylene alkylester, sorbitan alkylester, polyoxyethylene sorbitan alkylester and polyoxyethylene polyoxypropylene glycol.

In addition, cationic and amphoteric surface active agents may also be used as necessary. For example, a cationic surface active agent can be used in the case of mixing in a drug targeted at the rain-propagatingpathogen, *D. citri,* in the ingredients, an anionic surface active agent can be used in the case of mixing in a drug targeted at the air-propagating pathogen, *S. fuliginea,* in the ingredients, while a nonionic surface active agent can be used in the case of mixing in a drug targeted at the intermediate-propagating pathogen, *Pyricularia oryzae,* in the ingredients. These surface active agents may be used alone or as a combination of two or more types in an arbitrary ratio.

A preparation referred to in the present invention includes granules, tablets, packs, powders, capsules and so forth. Granules referred to in the present invention refer to that in which a solid composition in powdered form is formed into a granular form, the shape of which differs according to the granulation method, and of which various types exist ranging from those having a spherical shape to those having an irregular shape. The size of the granules ranges from about 100 to 10,000 μm, and preferably about 200 to 4,000 μm. In addition, tablets referred to in the present invention are that in which a powdered or granular composition is compressed and formed into a constant shape, of which there are various types ranging from those having a cylindrical shape to those having an irregular shape. Although the size of the tablets varies according to the method of their application, in the case of cylindrical tablets, the size is normally within the range of a diameter of about 5 to 100 mm and a thickness of about 1 to 50 mm, and the weight per tablet is about 0.1 to 300 g, preferably about 1 to 100 g, and more preferably about 5 to 50 g.

The effervescent preparation for plants of the present invention can dissolve in water followed by spraying, irrigating or immersing, and besides, tablets or granules, sowed by hand or a spreading machine, can be uniformly and directly applied. For example, when 2 to 200, and preferably 5 to 20, tablets per 10 acres are directly applied to a watered rice paddy, carbon dioxide gas is generated as a result of contact with the water, and yeast extract, methionine and so forth are rapidly dissolved and diffused in the rice paddy. Since the time required for that dissolution and diffusion is short at several minutes to several hours, in comparison with conventional application methods in which yeast extract is diluted with water in advance and then sprayed onto the stems and leaves, it is highly advantageous in terms of work, storage and transport since special machinery is not required and the preparation need only be thrown from a levee and so forth without having to enter the rice paddy directly.

In addition, the effervescent preparation for plants of the present invention can also be made into a sealed pack by packaging the above granules or tablets using a polymer film or water-soluble paper made of, for example, polyvinyl alcohol, carboxymethylcellulose or polyethylene glycol derivative.

There are no particular limitations on the production process of the effervescent preparation for plants of the present invention. More specifically, it can be produced with, for example, the process described below.

As an example of a production process of granules, a powdered solid composition containing required amounts of carbonate or hydrogencarbonate, water-soluble solid acid, yeast extract and/or methionine, and other auxiliary agents as necessary are uniformly mixed and crushed, formed into a sheet, pillow-shaped granules or slag using a roller compacter, briquetting machine or other type of dry granulating machine or slag machine and coarsely crushed with a grader to obtain granules having a particle size within the range of about 100 to 10,000 μm, and preferably about 200 to 4,000 μm.

In addition, although it is also possible to use a powdered solid composition prior to using a granulating machine, for example that having a particle size, for example, that allows the granules to sink in water, namely less than about 100 μm, directly in a field, in consideration of handling, it is preferable to use in the form of sealed packs containing the above powder by using a water-soluble polymer film or water-soluble paper made of, for example, polyvinyl alcohol, carboxymethylcellulose or polyethylene glycol derivative and so forth.

As an example of a process for producing tablets, a constant amount of the above powdered solid composition or the above granules is placed in a mortar followed by pounding into tablets. Tablets can also be obtained industrially by continuous press forming with a briquetting machine or tableting machine.

EMBODIMENTS

Although the following provides a detailed explanation of the embodiments of the present invention, the present invention is not limited. to these embodiments. Furthermore, the term "parts" in the following explanations indicates "parts by weight" in all cases.

Embodiment 1

Granule Production Example

Yeast extract was obtained in the manner shown below.

For pre-culturing, 50 ml of culture liquid [Yeast Nitrogen Base (Difco)+1% (W/V) glucose] was inoculated with one loopful of test yeast (Saccharomyces cerevisiae IFO-0234) and shake cultured overnight at 27° C. This yeast culture was then transferred to 950 ml of the above culture liquid for final culturing under the same conditions.

After culturing, the yeast culture was centrifuged for 5 minutes at 2000 rpm with a centrifuge. After removing the supernatant, sterilized distilled water was added to the sediment (yeast) after which the yeast were carefully suspended and centrifuged again under the same conditions. This procedure was repeated three times after which the sediment was washed to remove any remaining culture liquid.

Wet yeast (wet weight: 20 g) were suspended in 50 ml of 50% (V/V) ethanol and allowed to self-decompose while shake culturing overnight at 30–40° C.

Following completion of the above reaction, the suspension was filtered with a 0.45 μm membrane filter. The filtrate was spray-dried to obtain a yeast extract powder (composition: Table 1)

TABLE 1

| Analytical test parameter | Result | Analysis method |
| --- | --- | --- |
| Moisture | 5.0% | Normal pressure heat drying |
| Total amino acids | 57.8% | |
| Lipids | 0.1% | Soxhlet extraction |
| Fiber | 0% | Modified Henneberg -Stowman Method |
| Ash | 11.3% | Direct ashing |
| Saccharides | 18.5% | (Note 1) |
| Phosphorous | 1.32% | Vanadomolybdenic acid spectrophoto-metry |
| Iron | 5.67 mg/100 g | o-phenanthroline spectrophotometry |
| Calcium | 91.7 mg/100 g | Potassium permanganate volumetric method |
| Sodium | 597 mg/100 g | Atomic absorption photometry |
| Potassium | 4.905 | Atomic absorption photometry |
| Magnesium | 66.2 mg/100 g | Atomic absorption photometry |

Note 1: Calculation formula: 100 − (moisture + protein + lipid + fiber + ash)

10 parts of yeast extract obtained in the above manner, 35 parts of sodium hydrogencarbonate, 35 parts of citric acid and 20 parts of lactose were uniformly mixed. After mixing and crushing with a microsample mill (Hosokawa Kogyo Co., Ltd.), the powder was press formed with a roller compacter (Turbo Kogyo Co., Ltd.). After coarse crushing and grading, Granules A were obtained having a particle size of 500 to 2000 μm.

Embodiment 2

Tablet Production Example 10 parts of yeast extract obtained in the same manner as Embodiment 1, 35 parts of sodium hydrogencarbonate, 35 parts of citric acid, 5 parts of DL-methionine and 15 parts of lactose were uniformly mixed. After mixing and crushing with a microsample mill (Hosokawa Kogyo Co., Ltd.), 50 g of the composition were press formed using a tablet-making machine (Kikusui Co., Ltd.) to obtain Tablets B having a diameter of 50 mm and thickness of 16 mm.

Embodiment 3

Tablet Production Example 10 parts of yeast extract obtained in the same manner as Embodiment 1, 35 parts of sodium hydrogencarbonate, 35 parts of citric acid, 5 parts of urea and 15 parts of lactose were uniformly mixed followed by performing the same procedure as Embodiment 2 to obtain Tablets C weighing 50 g and having a diameter of 50 mm and thickness of 16 mm.

Embodiment 4

Tablet Production Example 10 parts of DL-methionine, 35 parts of sodium hydrogencarbonate, 35 parts of citric acid, 5 parts of urea and 15 parts of lactose were uniformly mixed followed by performing the same procedure as Embodiment 2 to obtain Tablets D weighing 50 g and having a diameter of 50 mm and thickness of 16 mm.

Comparative Example 1

10 parts of yeast extract obtained in the same manner as Embodiment 1 and 90 parts of lactose were uniformly mixed followed by performing the same procedure as Embodiment 1 to obtain Granules E having a particle size of 500 to 2000 μm.

Comparative Example 2

10 parts of yeast extract obtained in the same manner as Embodiment 1, 5 parts of DL-methionine and 85 parts of lactose were uniformly mixed followed by performing the same procedure as Embodiment 2 to obtain Tablets F weighing 50 g and having a diameter of 50 mm and thickness of 16 mm.

Comparative Example 3

10 parts of yeast extract obtained in the same manner as Embodiment 1, 5 parts of urea and 85 parts of lactose were uniformly mixed followed by performing the same procedure as Embodiment 2 to obtain Tablets G weighing 50 g and having a diameter of 50 mm and thickness of 16 mm.

Comparative Example 4

10 parts of DL-methionine, 5 parts of urea and 85 parts of lactose were uniformly mixed followed by performing the same procedure as Embodiment 2 to obtain Tablets H weighing 50 g and having a diameter of 50 mm and thickness of 16 mm.

[Dispersion Test]

200 liters of water were filled into a 200 liter tank having a diameter of 57 cm and height of 86 cm. 50 g aliquots of Granules A and Tablets B through D obtained in Embodiments 1 through 4 along with Granules E and Tablets F through H obtained in Comparative Examples 1 through 4 were respectively placed in the tank. 1000 ml of water were sampled from the top layer of the tank 30 minutes later followed by measurement of total amino acid and methionine levels. In addition, the samples were also examined for the presence of undissolved solid matter. Those results are shown in Table 2. In Table 2, theoretical values are calculated from the blended amounts, while measured values are the values obtained in the above dispersion test.

TABLE 2

| | | Total amino acids | | Methionine | | |
| --- | --- | --- | --- | --- | --- | --- |
| | | Theoretical value | Measured value | Theoretical value | Measured value | Solid matter |
| Emb. 1 | Granules A | 14.45 | 14.41 | — | — | No |
| Emb. 2 | Tablets B | 26.95* | 26.88* | 12.50 | 12.49 | No |
| Emb. 3 | Tablets C | 14.45 | 14.44 | — | — | No |
| Emb. 4 | Tablets D | — | — | 25.00 | 24.89 | No |
| Comp. Ex. 1 | Granules E | 14.45 | 10.11 | — | — | Small amount |
| Comp. Ex. 2 | Tablets F | 26.95* | 8.28* | 12.50 | 3.95 | Large amount |
| Comp. Ex. 3 | Tablets G | 14.45 | 4.01 | — | — | Large amount |
| Comp. Ex. 4 | Tablets H | — | — | 25.00 | 2.18 | Large amount |

Values indicated with an asterisk include methionine.

As is clear from Table 2, in the case of Granules A and Tablets B through D obtained in Embodiments 1 through 4, the yeast extract and methionine dissolved and diffused in a short time and there was no residual solid matter. In contrast, in the case of Granules E and Tablets F through H obtained in Comparative Examples 1 through 4, the yeast extract and methionine dissolved and diffused with difficulty and solid matter remained in the tank.

Test Example

Effect on Paddy Rice Yield

Water was filled into a rice paddy containing immature rice plants (25 days before the appearance of ears) to a water level of 5 cm from the ground surface after which Tablets D obtained in Embodiment 4 were uniformly thrown in at a ratio of 1 tablet (50 g) per are to investigate the yield at the time of harvest. Six varieties of rice were used, and the surface area of each test area was 40 acres. Those results are shown in Table 3.

TABLE 3

Effect on Paddy Rice Yield - Units: kg/10 a

| Variety | Untreated area | Tablet-treated area | Amount of increase |
| --- | --- | --- | --- |
| Hoshinoyume | 590 | 640 | +50 |
| Kirara 397 | 586 | 632 | +46 |
| Hitomebore | 589 | 605 | +16 |
| Koshihikari | 471 | 546 | +75 |
| Yamahoushi | 441 | 615 | +174 |
| Hinohikari | 452 | 522 | +70 |
| Average | 521.5 | 593.3 | +71.8 |

Based on Table 3, yield was observed to increase by 10% or more.

INDUSTRIAL APPLICABILITY

The effervescent preparation for plants of the present invention containing yeast extract and/or methionine and so forth can be easily dissolved and diffused when applying to a field, has good storage stability by being resistant to putrefaction and deterioration caused by contamination by sundry germs in comparison with the case of dissolving in water and so forth, is handled easily, and can be applied to watered rice paddies directly by throwing, thereby enabling shortening of working time and conservation of manpower.

What is claimed is:

1. An effervescent preparation for plants comprising a solid composition containing at least carbonate and/or hydrogen-carbonate, water-soluble solid acid, yeast extract and/or methionine, wherein the total content of carbonate, hydrogen-carbonate and water soluble solid acid is 10 to 90 weight percent and the weight ratio of carbonate and hydrogen-carbonate to water soluble solid acid is 3:7 to 7:3.

2. An effervescent preparation for plants as set forth in claim 1 that also contains at least one type of substance selected from the group consisting of an agricultural chemical active ingredient, a fertilizer ingredient and a surface active agent.

* * * * *